US006511650B1

United States Patent
Eiselt et al.

(10) Patent No.: US 6,511,650 B1
(45) Date of Patent: Jan. 28, 2003

(54) PREPARING POROUS HYDROGEL PRODUCTS

(75) Inventors: Petra Eiselt, Houston, TX (US); Craig Halberstadt, Charlotte, NC (US); David Mooney, Ann Arbor, MI (US); Julia Yeh, Ann Arbor, MI (US); Rachel Latvala, Ann Arbor, MI (US); Jon A. Rowley, Chapel Hill, NC (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 09/958,376

(22) PCT Filed: Apr. 10, 2000

(86) PCT No.: PCT/US00/09466

§ 371 (c)(1),
(2), (4) Date: Apr. 18, 2002

(87) PCT Pub. No.: WO00/61668

PCT Pub. Date: Oct. 19, 2000

Related U.S. Application Data (60) Provisional application No. 60/128,681, filed on Apr. 9, 1999.

(51) Int. Cl.[7] ............................ A61L 15/42; A61L 25/00
(52) U.S. Cl. ............................ 424/44; 424/45; 424/485; 424/488; 424/489; 424/499; 424/500; 521/182; 521/189; 521/84.1
(58) Field of Search ............................ 424/44, 45, 485, 424/488, 489, 499, 500; 521/182, 185, 84.1

(56) References Cited

U.S. PATENT DOCUMENTS

| 4,948,575 | A | * | 8/1990 | Cole et al. |
| 5,451,613 | A | * | 9/1995 | Smith |
| 5,750,585 | A | * | 5/1998 | Park et al. |
| 5,948,829 | A | * | 9/1999 | Wallajepet et al. |
| 2001/0038831 | A1 | * | 11/2001 | Park et al. |
| 2001/0046518 | A1 | * | 11/2001 | Sawhney |

* cited by examiner

*Primary Examiner*—Morton Foelak
(74) *Attorney, Agent, or Firm*—Millen, White, Zelano & Branigan, P.C.

(57) ABSTRACT

This invention is directed to a new approach to form porous hydrogel materials by first creating gas pockets in the gel and then removing this gas. The removal of the gas creates a porous material, and the initial incorporation of sufficient gas allows one to create a material with an open, interconnected pore structure. Advantageous features of the resulting materials, in addition to their interconnected pore structure, may include that the pore structure is maintained over extended time periods and that the gels maintain a high mechanical integrity that allows seeding with cells and implantation without destruction or compression of the material.

17 Claims, 1 Drawing Sheet

FIG. 1a

FIG. 1b

PREPARING POROUS HYDROGEL PRODUCTS

This application claims priority of provisional application Serial No. 60/128,681, filed Apr. 9, 1999, the entire contents of which are incorporated by reference herein.

Alginate and other hydrogels are attractive materials for a variety of biomedical applications, including cell transplantation, and drug delivery. In many of these applications one desires to either seed cells into the material, or allow for cellular invasion following implantation into the body. However, alginate is typically used in the physical form of a hydrogel, with small pores (nm size scale) that do not allow for cell movement in or out of the material. This invention is directed to a new approach to form porous hydrogel materials by first creating gas pockets in the gel and then removing this gas. The removal of the gas creates a porous material, and the initial incorporation of sufficient gas allows one to create a material with an open, interconnected pore structure. Advantageous features of the resulting materials, in addition to their interconnected pore structure, may include that the pore structure is maintained over extended time periods and that the gels maintain a high mechanical integrity that allows seeding with cells and implantation without destruction or compression of the material.

The invention is in contrast to other processing approaches typically used to achieve a porous structure with these types of materials (e.g., lyophilization) in which the porous nature is lost as the material rehydrates and/or the material is significantly weakened by the process.

An approach to form and subsequently remove gas bubbles from alginate gels has been previously described (Gotoh et al., *Cytotechnology* 11, 35 (1993)). However, the methods described in this article did not lead to the formation of structures with a sufficient degree of porosity or a sufficiently open interconnected pore structure.

The method described herein is a considerable modification of the Gotoh et al. method and is conducted under conditions outside of the ranges described therein. An object of the invention is to provide biocompatible hydrogel materials, for example alginate materials, which have a significantly macroporous and open pore structure, e.g., such that the pores are sufficiently open and sized to allow cellular transport therein. This facilitates vascularization and structural integration with the surrounding tissue when used in tissue engineering applications. Thus, the macroporous hydrogel will preferably have pores of at least 1 $\mu$m, particularly from 10 to 1000 $\mu$m. While not limited thereto, the overall porosity is preferably from 30 to 90%, more preferably 35 to 75%. The total surface accessible interconnected porosity is preferably from 30–80%, more preferably 35–70%.

Upon further study of the specification and appended claims, further objects and advantages of this invention will become apparent to those skilled in the art.

Objects according to the invention can be achieved by a method for preparing a hydrogel material having macroporous open pore porosity, which comprises:

a) providing a solution of a hydrogel-forming material, a surfactant and, optionally, a gas-generating component which solution is capable of being mixed in the presence of a gas (either added or generated by the gas-generating component) to incorporate the gas in the solution and form a stable foam;

b) forming a stable foam by mixing the solution in the presence of a gas and/or, if the gas-generating component is present, by subjecting the solution to conditions or agents which result in generation of gas from the gas-generating component;

c) exposing the stable foam to conditions and/or agents which result in gelling of the hydrogel-forming material to form a hydrogel containing gas bubbles therein;

d) releasing the gas bubbles from the hydrogel, for example by subjecting it to a vacuum, to form a hydrogel material having macroporous open pore porosity.

Steps b) and c) may be performed simultaneously or in series.

Any hydrogel-forming material which can provide the desired effect of resulting in a foam which allows preparation of the open pore material can be used in the invention. Examples of materials which can form hydrogels include polylactic acid, polyglycolic acid, PLGA polymers, alginates and alginate derivatives, gelatin, collagen, agarose, natural and synthetic polysaccharides, polyamino acids such as polypeptides particularly poly(lysine), polyesters such as polyhydroxybutyrate and poly-$\epsilon$-caprolactone, polyanhydrides; polyphosphazines, poly(vinyl alcohols), poly(alkylene oxides) particularly poly(ethylene oxides), poly(allylamines)(PAM), poly(acrylates), modified styrene polymers such as poly(4-aminomethylstyrene), pluronic polyols, polyoxamers, poly(uronic acids), poly(vinylpyrrolidone) and copolymers of the above, including graft copolymers.

A preferred material for the hydrogel is alginate or modified alginate material. Alginate molecules are comprised of (1–4)-linked $\beta$-D-mannuronic acid (M units) and ($\alpha$-L-guluronic acid (G units) monomers which vary in proportion and sequential distribution along the polymer chain. Alginate polysaccharides are polyelectrolyte systems which have a strong affinity for divalent cations (e.g. $Ca^{+2}$, $Mg^{+2}$, $Ba^{+2}$) and form stable hydrogels when exposed to these molecules. See Martinsen A., et al., *Biotech. & Bioeng.*, 33 (1989) 79–89. Calcium cross-linked alginate hydrogels have been used in many biomedical applications, including materials for dental impressions (Hanks C. T., et al., *Restorative Dental Materials*; Craig, R. G., ed., Ninth Edition, Mosby (1993)), wound dressings (Matthew I. R. et al., *Biomaterials*, 16 (1995) 265–274), an injectable delivery medium for chondrocyte transplantation (Atala A., et al., *J Urology*, 152 (1994) 641–643), and an immobilization matrix for living cells (Smidsrod O., et al, TIBTECH 8 (1990) 71–78).

An alternative embodiment utilizes an alginate or other polysaccharide of a lower molecular weight, preferably of size which, after dissolution, is at the renal threshold for clearance by humans. Preferably, the alginate or polysaccharide is reduced to a molecular weight of 1000 to 80,000 daltons, more preferably 1000 to 60,000 daltons, particularly preferably 1000 to 50,000 daltons. It is also useful to use an alginate material of high guluronate content since the guluronate units, as opposed to the mannuronate units, provide sites for ionic crosslinking through divalent cations to gel the polymer.

Alginate can be $\gamma$-irradiated in a controlled fashion to cause a random fission of the polymer chains and generation of appropriate low molecular weight alginate fragments [Hartman et al., Viscosities of cacia and sodium alginate after sterization by cobald-60. J. Pharm. Sci.; 1975, 64(5): 802–805; King K., Changes in the functional properties and molecular weight of sodium alginate following $\gamma$-irradiation. Food Hydrocoll. 1994; 8(2): 83–96; Delincée H., Radiolytic effects in food. In: Proceedings of the international workshop on food irradiation. 1989, p 160–179]. In these earlier descriptions of the degradation of alginate utilizing γ-irradiation, the conditions used were outside the range required to generate materials with molecular weights lower than 200 kD, or they were used on alginate solutions rather than the bulk material. Other methods for the controlled degradation of alginate are also available [Kimura et al., Effects of soluble alginate on cholesterol excretion and glucose tolerance in rats. J. Ethnopharn.; 1996, 54: 47–54; Purwanto et al., Degradation of low molecular weight fragments of pectin and alginates by gamma-irradiation. Acta Alimentaria; 1998, 27(1): 29–42], but γ-irradiation is a reliable and simple technique for generating low molecular alginates. The reduction in molecular weight can also be effected by hydrolysis under acidic conditions or by oxidation, to provide the desired molecular weight. The hydrolysis may be conducted in accordance with a modified procedure of Haug et al. (Acta. Chem. Scand., 20, p. 183–190 (1966), and Acta. Chem. Scand., 21, p. 691–704 (1967)), which results in a sodium poly(guluronate) of lower molecular weight which is essentially absent of mannuronic acid units. The oxidation to lower molecular weight is preferably conducted with a periodate oxidation agent, particularly sodium periodate; see PCT/US97/16890.

As expected, alginate solutions prepared from lower molecular weight alginates possessed decreased viscosities, and more concentrated solutions were required to form stable foams. The difference in the total void volume of beads formed from low and high molecular weight alginate is likely caused by the increased alginate concentration required to form stable foams in the low molecular weight alginates.

For alginate materials, it is preferred to use starting solutions of alginate salt in an amount, for example, of 3 to 10% w:w (weight based on weight of water), more preferably 3 to 5% w:w. For other materials,. the amount used in the starting solution will depend upon the material used, however, it is preferred to use at least 3% w:w in the starting solution. This will preferably result in concentrations of the alginate or other hydrogel-forming material in the solution to be foamed of more than 3% weight, particularly 3–10%, more particularly, 3–5%.

The hydrogel-forming material is the precursor, ungelled form of the hydrogel. It will be a soluble form of the hydrogel which is capable of being gelled by application of some condition or agent. For example, alginate salts, such as sodium alginate, are gelled in the presence of divalent cations, such as calcium present in calcium chloride. Other materials may be gellable by a change in pH or temperature, for example.

As the surfactant, any surfactant which will facilitate formation and stabilization of gas bubbles in the solution, without preventing the other steps of the method, can be used. Useful examples thereof include bovine serum albumin (BSA), the pluronic class of surfactants (e.g., F108 and F68), polyethylene glycol and propylene glycol alginate surfactants. The amount of surfactant used will depend on the amount and type of the hydrogel being formed and an amount which facilitates formation and stabilization of gas bubbles in the solution, without preventing the other steps of the method, can be used.

Particularly preferred are the pluronics surfactants, as the bovine albumin originally used may elicit a foreign body response in vivo. Pluronics are non-ionic surfactants and their foaming properties increase with increasing ethylene oxide content. A similar trend is observed as the molecular weight of the hydrophobic portion increases at a fixed ethylene oxide content (Alexandridis et al., Micellization of poly(ethylene oxide)-poly(propylene oxide)-poly(ethylene oxide) triblock copolymers in aqueous solutions: thermodynamics of copolymer association. Macromolecules; 1994, 27: 2414–2425.) The particular pluronics, F108 and F68, possess the same ethylene oxide content (80% (w/w)) but differ in average molecular weight (14,600 and 8,400 Daltons, respectively). The increased porosity of beads formed with F108 is consistent with its foaming ability as compared to beads formed with F68. It is also known that pluronics surfactants do not micellize at a critical micelle concentration (CMC) but instead aggregate over a wide range of concentrations (ACR). The limiting aggregation concentration (LAC) is the point at which the surfactant reaches saturation, which corresponds to the more conventional CMC. The ACR for F108 ranges from 400–50,000 ppm (see Alexandridis cited above). The LAC or CMC for this surfactant has been reported to be >50,000 ppm or 4.5% w/v, respectively (see Aexandridis cited above). Thus, it seems plausible that a high surfactant concentration can lead to premicellar aggregates, which directly effect the porosity determined in the beads.

In a particularly preferred embodiment, the hydrogel-forming material is a low molecular weight alginate and the surfactant is a pluronics surfactant.

For use of BSA as the surfactant, the method may be conducted using a BSA concentration in the final solution to be foamed of 0.05–1% weight. The amount used will depend on the amount of the algifiate or other hydrogel material used. A BSA stock solution of 1 to 10% weight BSA in water can be used for this purpose. For example, using 2 grams of a 3 to 5% w:w of alginate, 240 to 400 mg of a 15% solution of BSA has been found useful. The weight ratio of BSA to alginate may be from 1:10 to 1:60, preferably 1:10 to 1:20, for some applications, but it is not limited thereto.

If a gas-generating component is provided, it is preferred to use sodium bicarbonate, which will release carbon dioxide gas when exposed to a mild acid, for example, acetic acid. For this purpose, a 10% volume acetic acid solution may be used which provides at least an amount of acetic acid equimolar to the amount of carbon dioxide to be released from the sodium bicarbonate. For example, the bicarbonate can be added in powder form or as a bicarbonate solution of 1.0M to 2.0M to provide a concentration of 0.5 to 5.0% weight in the solution to be foamed. When using an alginate hydrogel and a BSA surfactant, it has further been found that the ratio of BSA to bicarbonate has an effect on the product. It is preferred in this case that the weight ratio of 15% weight BSA solution to the 1.0 to 2.0M bicarbonate solution is 2:1 to 1:1. Other materials which release gases upon application of some condition or agent may be used provided they will result in formation of gas bubbles in the hydrogel which are releasable upon application of a vacuum and do not otherwise interfere in the preparation.

A gas-generating component may not be necessary if the solution of hydrogel-forming material and surfactant can be mixed in the presence of gas to provide suitable gas bubbles in the resulting hydrogel. Preferably the solution is mixed in the presence of air to result in the foaming and subsequent formation of air bubbles when the hydrogel is gelled. When a gas-generating component is used, the hydrogel may have gas bubbles of air provided by the mixing as well as gas bubbles generated by the gas-generating component. Any mixing means which results in adequate foaming can be used.

The stable foam resulting from mixing of the above-described solution is gelled in a manner dependent upon the hydrogel-forming material, e.g., by contact with a gelling agent or a change in pH or temperature. For alginate hydrogels, the gelling is effected by contact with divalent cations in solution, e.g., a calcium chloride solution of from 0.1 to 1.0M, preferably about 0.5M. The divalent cations serve to jonically crosslink the alginate. The manner of exposing the solution to the gelling agent or condition will depend on the desired shape of resulting porous hydrogel material. For example, hydrogel beads can be provided by adding the stable foam dropwise to a solution of the gelling agent, such as through a syringe or a syringe pump for scaled up applications. In a similar manner, the stable foam may be provided continuously through a syringe device to provide the porous hydrogel in a fibrous form. The stable foam may also be cast in a desired shape and subject to the gelling agent or gelling condition to provide a shaped article, which may be particularly useful for tissue regeneration applications. Other forms of the material may be prepared using means available in the art.

The resulting hydrogel will contain gas bubbles and exposure thereof to a vacuum will draw out the entrapped gas bubbles to create an open pore macroporous hydrogel.

In one preferred embodiment, the process involves first providing a solution of sodium alginate in water. Sodium bicarbonate and bovine serum albumin (BSA) are then added to this solution and mixed to allow for incorporation of air bubbles in the resulting solution to create a stable foam. This solution is then placed in a syringe and extruded dropwise into a stirred solution of calcium chloride and acetic acid in water (gelling solution). The calcium ions serve to gel the alginate, while the acetic acid reacts with the bicarbonate to generate carbon dioxide gas in the hydrogel. The gelled alginate in the form of microbeads is collected separately from the solution. The alginate is subsequently exposed to a vacuum to draw out the entrapped gas bubbles (both of air and carbon dioxide) and create the open pore structure.

It is important to note that as the hydrogel is varied the specific, optimal conditions may vary as well. For example, utilization of a lower molecular weight alginate will decrease the solution viscosity, necessitating a higher alginate concentration and/or higher surfactant concentration, and vice versa. Varying the guluronic acid content of the alginate will alter the strength of the hydrogel and require either an increased vacuum to remove gas bubbles or a decreased starting. alginaie concentration.

The materials prepared by the process of the invention exhibit a wide range of utilities. They may be applied to any use which requires a porous hydrogel material, particularly with an open pore structure.: For instance, the materials are useful as matrices or scaffolds into which cells can migrate, the cells being compatible therein and growing to achieve their intended function, such as in tissue replacement, eventually replacing the matrix depending on its biodegradability. Furthermore, the materials can be used to provide matrices already bound to cells, which may then be surgically implanted into a body. Further, the materials can be used as a sustained release drug delivery system, as wound healing matrix materials, as matrices for in vitro cell culture studies or uses similar thereto. The stable structure of the materials of the invention provides ideal cell culture conditions.

The materials of the invention may also have application in cell transplantation, including for hepatocytes (see, D. J. Mooney, P. M. Kaufmann, K. Sano, K. M. McNamara, J. P. Vacanti, and R. Langer, "Transplantation of hepatocytes using porous biodegradable sponges," Transplantation Proceedings, 26, 3425–3426 (1994); D. J. Mooney, S. Park, P. M. Kaufrnann, K. Sano, K. McNamara, J. P. Vacanti, and R. Langer, "Biodegradable sponges for hepatocyte transplantation," Journal of Biomedical Materials Research, 29, 959–965 (1995)), chondrocytes and osteoblasts (see, S. L. Ishaug, M. J. Yaszemski, R. Biciog, A. G. Mikos; "Osteoblast Function on Synthetic Biodegradable Polymers", J. of Biomed. Mat. Res., 28, p. 1445–1453 (1994)).

Smooth muscle cells may readily adhere to the material prepared according to the invention and create three-dimensional tissues especially if appropriate cell adhesion ligand are coupled to the hydrogel structure within these porous structures; thus, they provide a suitable environment for cell proliferation. In addition, these materials have potential to incorporate growth factors.

Another useful application for the polymer matrices of the invention is for guided tissue regeneration (GTR). This application is based on the premise that progenitor cells responsible for tissue regeneration reside in the underlying healthy tissue and can be induced to migrate into a defect and regenerate the lost tissue. A critical feature of materials for GTR is the transport of cells into the material, a property which is dictated by the pore size distribution and pore continuity, i.e., interconnectivity. The material must allow the desired cells to invade the material while preventing access to other cell types.

The entire disclosure of all applications, patents and publications, cited above and below, is hereby incorporated by reference.

In the foregoing and in the following examples, all temperatures are set forth uncorrected in degrees Celsius; and, unless otherwise indicated, all parts and percentages are by weight.

EXAMPLES

Materials

Sodium alginate (MVG) was purchased from Pronova Biopolymers, Inc. (Portsmouth, N.J.) with an overall guluronic acid (G-block) content of approx. 70%, as reported by the manufacturer. Sodium bicarbonate and calcium chloride were furnished by Fisher Scientific (Pittsburgh, Pa.), and ethanol (95%) was from McComnick Distilling Company, Inc. (Weston, Mo.). Pluronics F68 and F108 were provided from BASF Corporation (Mount Olive, N.J.). 3-(4,5-dimethylthiazol-2-yl-2,5-diphenyl tetrazolium bromide) (MTT), glacial acetic acid, bovine serum albumin fraction V (BSA), hematoxylin, eosin, and 10% neutral buffered formalin were received from Sigma (St. Louis, Mo.). Phosphte-buffered saline (PBS pH=7.2), fetal bovine serum (FBS), Dulbecco's Modified Eagles Medium (DMEM), and penicillin-streptomycin were purchased from Life Technologies (Grand Island, N.Y.). All chemicals were used as received.

Methods

GPC Measurements

Molecular weights and distributions we determined at room temperature using a system equipped with an isocratic pump (P1000, Thermo Separation Products) and a triple detector system (Viscotek), including a laser refractometer (LR 40) and a dual detector (T60, differential viscometer and RALLS). 0.1 M $NaNO_3$ buffer solution (pH 6.3) was used as mobile phase, and the flow rate was 0.7 ml/min. A set of two TSK-gel columns (G4000$PW_{XL}$ and G3000 $PW_{XL}$) was used. The samples were dissolved in the mobile phase, filtered, and injected through a Rheodyne valve (Model 7010) equipped with a 100 $\mu$l injection loop.

Example 1 (comparative)

The conditions described in the previously described Gotoh publication were first investigated to determine if they could be used to create porous alginate matrices. The conditions described in the previous publication which were claimed to be required for formation of porous alginate were:

Starting solutions
   alginate: 1–1.5% (w: w)
   BSA: 0.01–0.03% (w: w)
   sodium bicarbonate: 0.1–0.5M
Gelling solution
   0.1M calcium chloride
   10% (v:v) acetic acid We first utilized a number of conditions within these ranges in an effort to fabricate porous beads, but no combinations of these conditions led to the formation of a porous structure with an interconnected pore structure. It is important to note that alginates with comparable properties to those utilized in the original description were used in these studies. The alginate used has a guluronic acid content of approximately 70% and a molecular weight of 190 kD.

We specifically utilized the following combinations of variables with negative results:
1. Starting solutions of 1.5 w:w % alginate, 0.5M bicarbonate, 0–1.5% BSA (examined wide range of BSA concentrations in this range) resulted in no formation of foamy solution (indicating no gas bubbles in solution)
2. Starting solutions of 1.0–1.5 w:w % alginate, 2.0M bicarbonate, 0.5–1.5% BSA resulted in no formation of foamy solution (indicating no gas bubbles in solution)

Example 2 (Comparative)

A range of conditions outside of the previously described conditions were also investigated that did not lead to the formation of porous, interconnected structures.
1. Starting solutions of 1.5–5.0 w:w % alginate, 2.0M bicarbonate, 0.5–1.0% BSA resulted in no formation of foamy solution (indicating no gas bubbles in solution)

Example 3

Based on the negative results found in the first two examples, it was concluded that the two critical aspects for this process to work are gas bubble formation and subsequent stabilization. For embodiments using BSA surfactant and a bicarbonate gas-generating component, a certain ratio of BSA to bicarbonate solution is necessary to develop a foamy solution. Stabilization of the gas bubbles is dependent on the viscosity of the starting alginate solution and the concentration of BSA. A low viscosity solution cannot stabilize entrapped gas bubbles, while too high of a viscosity leads to a gel that is so strong that the gas bubbles cannot be readily removed during the vacuum step. In addition, the BSA serves to stabilize the gas bubbles in the alginate solution, and it is critical to have the appropriate BSA concentration to enable formation of a stable foam containing gas bubbles.

Specifically, the following conditions did lead to the formation of open, interconnected porous hydrogels.
1. 3 w:w % alginate, 2.0M bicarbonate and 1.5% BSA were used as the starting solutions. 2 g of the alginate solution were mixed with 0.24 g of the BSA solution and 0.12 g of the bicarbonate solution to yield a foamy solution.
2. 3 w:w % alginate, 2.0M bicarbonate and 1.5% BSA were used as the starting solutions. 2 g of the alginate solution were mixed with 0.24 g of the BSA solution and 0.24 g of the bicarbonate solution to yield a foamy solution.
3. 4 w:w % alginate, 2.0M bicarbonate and 1.5% BSA were used as the starting solutions. 2 g of the alginate solution were mixed with 0.32 g of the BSA solution and 0.16 g of the bicarbonate solution to yield a foamy solution.
4. 4 w:w % alginate, 2.0M bicarbonate and 1.5% BSA were used as the starting solutions. 2 g of the alginate solution were mixed with 0.34 g of the BSA solution and 0.34 g of the bicarbonate solution to yield a foamy solution.
5. 5 w:w % alginate, 2.0M bicarbonate and 1.5% BSA were used as the starting solutions. 2 g of the alginate solution were mixed with 0.4 g of the BSA solution and 0.2 g of the bicarbonate solution to yield a foamy solution.
6. 5 w:w % alginate, 2.0M bicarbonate and 1.5% BSA were used as the starting solutions. 2 g of the alginate solution were mixed with 0.4 g of the BSA solution and 0.4 g of the bicarbonate solution to yield a foamy solution.
7. 5 w:w % alginate, 1.0M bicarbonate and 1.5% BSA were used as the starting solutions. 2 g of the alginate solution were mixed with 0.4 g of the BSA solution and 0.2 g of the bicarbonate solution to yield a foamy solution.

In sum, the following ranges of conditions were found preferable for forming interconnected pore structures by this embodiment:

Starting solutions of 3, 4 and 5 w:w % (weight % based on weight of water) alginate with 1.5% BSA and 1.0M to 2.0M bicarbonate solutions lead to the development of foamy solutions. The weight ratio of the BSA solution to the bicarbonate solution is preferably from 2:1 to 1:1. Their amounts used depend on the concentration of the alginate solution.

Example 4

We also used propylene glycol alginate as a surfactant in order to replace the protein BSA.
1. Equal amounts of alginate and propylene glycol alginate were dissolved in dd water to yield a 3% w:w solution. 2 g of this solution were mixed with 0.12 g of a bicarbonate solution to yield a foamy solution.

Example 5

We also changed the composition of the gelling solution in comparison to Gotoh. The reported 0.1 M $CaCl_2$ in Gotoh containing 10 vol % acetic acid did not lead a fast enough gelling of the alginate. The beads appeared sticky and beads tend to fuse together when in contact with other beads. The concentration of the $CaCl_2$ was raised to 0.5 M.

Example 6

An indication of the porosity of the beads formed in example 3 was obtained by observing beads suspended in an aqueous solution. Beads prior to exposure to vacuum appear opaque and float on the surface (indicating a low density as one would expect from the large amount of entrapped gas). Following exposure to vacuum, the beads appear clear and sink to the bottom of the solution (indicating an increased density due to replacement of the gas with the more dense aqueous solution).

Example 7

The porosity of beads formed in example 3 were visually examined to confirm their porosity. Following isolation of beads from the gelling solution, a large number of gas bubbles could be observed within the alginate matrices. Following removal of the gas bubbles, an open porous structure was observed.

Example 8

The interconnected pore structure of the matrices was assessed by seeding a solution of suspended cells onto porous alginate beads, and subsequently visualizing these cells using a, MTT (3-(4,5-dimethylthiazol-2-yl-2,5-diphenyl tetrazolium bromide) assay. In brief, 3T3 fibroblasts were suspendedin Dulbecco's Modified Eagles Medium (2 million cells/ml). Alginate beads were removed from their aqueous solution, and blotted onto paper to allow the water within the pores to be removed by capillary action. The beads were then placed in the cell suspension. After 1 hour, beads were removed from the cell suspension, and washed with medium. The beads were placed in medium containing 0.5 mg/ml MTT. MTT is taken up by cells and reduced in the mitochondria to an insoluble blue product that can be readily visualized with microscopic examination. Non-porous beads will not take up cells and thus no stained cells will be present within beads that do not contain large pores (greater than approximately 10 microns in diameter). Matrices which are porous will take up cells, and the distribution of dyed cells allows confirmation of the amount of interconnected pores in the matrix.

Example 9

To determine whether the pore structure remained stable over time, porous beads were allowed to remain in an aqueous solution for varying periods of time (1 day to 2 weeks) and subsequently analyzed for porosity by seeding cells and visualizing as in example 8. The incorporation and distribution of cells, and thus the matrix porosity, was unchanged following storage.

Example 10

To determine if the pore structure remained intact in vivo, porous alginate beads were transplanted into subcutaneous pockets of rats. The beads were harvested after 1 and 2 weeks, fixed, sectioned and stained with hematoxylin and eosin. Invasion of macrophages and fibroblasts was noted throughout the matrices at one week, with more cells being present and greater new collagen deposition in the beads by the invading cells by two weeks. This result confirms that the porous beads maintained their structure and allowed cell invasion in vivo. The beads maintained their original shape and dimensions, indicating that their mechanical properties were sufficient to withstand the compressional forces exerted in vivo.

Example 11

The process to fabricate porous alginate matrices has been scaled up to allow large quantities of these materials to be produced. To incorporate air bubbles in large volumes of the initial solution, the solution is vigorously mixed in a high speed mixer (e.g., Sunbeam hand mixer, Model 2485). A syringe pump is used to generate large numbers of reproducibly sized beads in a semi-automatic fashion.

Example 12

It is highly desirable for a variety of biomedical applications to prepare materials which are porous but also show degradation after implantation. One major drawback of alginates is their lack of degradability in vivo. Mammals don't carry the appropriate enzyme necessary to degrade alginate and the hydrolytical degradation at physiological conditions can only be considered minimal. One attractive alternative is the use of alginates with an average nmolecular weight low enough to allow the excretion of the material through the kidneys. This molecular weight is usually considered to lay around 50 kD.

Thus, we have investigated the controlled degradation of alginates to generate materials with a molecular weight below 50 kD, utilizing acid hydrolysis (solution), heat treatment (solution and bulk) and γ-irradiation (solution and bulk). The characteristics of the low molecular weight alginate fragments with respect to their weight average- and number average molecular weights ($M_w$ and $M_N$), and their polydispersity index were determined using GPC (gel permeation chromatography) and are shown in the following tables.

Preparation of low Molecular Weight Alginates

1. Acid Hydrolysis

Alginate solutions (2% (w:w)) were refluxed in 0.3 M HCl for various times. Subsequently, the molecular weights of the autoclaved samples were determined by GPC measurements. The gelling behavior of the autoclaved polymers was also determined. All samples were gelled in the presence of calcium ions.

TABLE 1

Alginate solutions degraded via hydrolysis in 0.3 M HCl.

| Sample | Time (min) | $M_N$ (g/mol) | $M_w$ (g/mol) | PDI | $W_f^1$ | Gelling[2] |
|---|---|---|---|---|---|---|
| Alg 2% | 3 | 9190 | 218200 | 23.7 | 0.30 | (+) |
| Alg 2% | 10 | 30100 | 115800 | 3.9 | 0.41 | (+) |
| Alg 2% | 20 | 18400 | 38400 | 2.1 | 0.70 | (+) |
| Alg 2% | 30 | 10300 | 15700 | 1.5 | 0.97 | (+) |
| Alg 2% | 40 | 5350 | 16900 | 3.2 | 0.97 | (+) |

[1]Weight fraction of polymer with average molecular weight ≦ 50 kD.
[2]Ionic cross-linking in 0.03 M $CaCl_2$.

2. Heat Treatment

Alginate (solution and bulk) were autoclaved (1.034 bar, 121° C.) to generate alginate with lower average molecular weights. Samples were autoclaved for 1 h, 2 h and 2.5 h, respectively. Subsequently, the molecular weights of the autoclaved samples were determined by GPC measurements. The gelling behavior of the autoclaved polymers was also determined. All samples gelled in the presence of calcium ions.

TABLE 2

Alginate (solution and bulk) degraded via heat treatment at 121° C. and 1.034 bar.

| Sample | Time (h) | $M_N$ (g/mol) | $M_w$ (g/mol) | PDI | $W_f^1$ | Gelling[2] |
|---|---|---|---|---|---|---|
| Alg 2% | 1 | 30100 | 112800 | 3.8 | 0.39 | (+) |
| Alg 2% | 2 | 28200 | 65500 | 2.3 | 0.55 | (+) |
| Alg 2% | 2.5 | 27300 | 47800 | 1.8 | 0.70 | (+) |
| Alg 3% | 1.25 | 57900 | 143500 | 2.5 | 0.25 | (+) |
| Alg 3% | 2.5 | 31200 | 85600 | 2.7 | 0.42 | (+) |
| Alg 8% | 2.5 | 1970 | 4900 | 2.5 | 1.00 | (+) |
| Alg bulk | 1 | 35300 | 107400 | 3.0 | 0.32 | (+) |
| Alg bulk | 2 | 11800 | 21800 | 1.9 | 0.96 | (+) |
| Alg bulk | 2.5 | 11100 | 17800 | 1.6 | 0.98 | (+) |

[1]Weight fraction of polymer with average molecular weight ≦ 50 kD.
[2]Ionic cross-linking in 0.03 M $CaCl_2$.

3. γ-irradiation

Alginate could be degraded through gamma irradiation at a variety of conditions. Subsequently, the molecular weights of the autoclaved samples were determined by GPC measurements. The first set of experiments (Table 3) was carried out by irradiation of alginate solutions (2 and 3%). The gelling behavior of the irradiated polymers was also determined. All samples gelled in the presence of calcium ions.

TABLE 3

Degradation of alginate solutions through gamma irradiation.

| Sample | Gamma Dose (Mrad) | Irradiation Time (min) | Dosage (Mrad/h) | $M_N$ (g/mol) | $M_W$ (g/mol) | PDI | exit $W_f^1$ | Gelling[2] |
|---|---|---|---|---|---|---|---|---|
| Alg 3% | 0.27 | 9 | 1.8 | 35300 | 80400 | 2.3 | 0.50 | (+) |
| Alg 3% | 0.51 | 17 | 1.8 | 19200 | 52900 | 2.8 | 0.64 | (+) |
| Alg 3% | 1.01 | 34 | 1.8 | 14400 | 33100 | 2.4 | 0.82 | (+) |
| Alg 2% | 1.52 | 50 | 1.8 | 9220 | 13800 | 1.5 | 1.00 | (+) |
| Alg 2% | 1.82 | 60 | 1.8 | 7080 | 11100 | 1.6 | 1.00 | (+) |
| Alg 2% | 1.50 | 93 | 1.0 | 6810 | 13400 | 2.0 | 0.98 | (+) |
| Alg 2% | 1.81 | 112 | 1.0 | 6840 | 13400 | 1.7 | 1.00 | (+) |

[1]Weight fraction of polymer sample with average molecular weight $\leq$ 50 kD.
[2]Ionic cross-linking in 0.03 M $CaCl_2$ solution.

TABLE 4

Degradation of alginate powder through gamma irradiation at a constant gamma dose.

| Sample | Gamma Dose (Mrad) | Irradiation Time (min) | Dosage (Mrad/h) | $M_N$ (g/mol) | $M_W$ (g/mol) | PDI | $W_f^1$ | Gelling[2] |
|---|---|---|---|---|---|---|---|---|
| Alg bulk | 0.27 | 9 | 1.8 | 15500 | 72500 | 4.7 | 0.50 | (+) |
| Alg bulk | 0.25 | 17 | 0.9 | 13500 | 96400 | 7.1 | 0.41 | (+) |
| Alg bulk | 0.26 | 39 | 0.4 | 18000 | 88800 | 4.9 | 0.43 | (+) |
| Alg bulk | 0.25 | 75 | 0.2 | 22200 | 205600 | 9.3 | 0.39 | (+) |
| Alg bulk | 0.25 | 150 | 0.1 | 41500 | 72200 | 1.8 | 0.42 | (+) |

[1]Weight fraction of polymer sample with average molecular weight $\leq$ 50 kD.
[2]Ionic cross-linking in 0.03 M $CaCl_2$ solution.

TABLE 5

Degradation of alginate powder through gamma irradiation at a constant irradiation time.

| Sample | Gamma Dose (Mrad) | Irradiation Time (min) | Dosage (Mrad/h) | $M_N$ (g/mol) | $M_W$ (g/mol) | PDI | $W_f^1$ | Gelling[2] |
|---|---|---|---|---|---|---|---|---|
| Alg bulk | 2.0 | 68 | 1.8 | 7670 | 40200 | 5.2 | 0.72 | (+) |
| Alg bulk | 1.0 | 68 | 0.9 | 18700 | 65200 | 3.5 | 0.55 | (+) |
| Alg bulk | 0.45 | 68 | 0.4 | 33600 | 153900 | 4.6 | 0.33 | (+) |
| Alg bulk | 0.09 | 68 | 0.08 | 28700 | 102700 | 3.6 | 0.35 | (+) |

[1]Weight fraction of polymer sample with average molecular weight $\leq$ 50 kD.
[2]Ionic cross-linking in 0.03 M $CaCl_2$ solution.

TABLE 6

Degradation of alginate powder through gamma irradiation at a constant irradiation dosage.

| Sample | Gamma Dose (Mrad) | Irradiation Time (h) | Dosage (Mrad/h) | $M_N$ (g/mol) | $M_W$ (g/mol) | PDI | $W_f^1$ | Gelling[2] |
|---|---|---|---|---|---|---|---|---|
| Alg bulk | 8.0 | 4.53 | 1.8 | 9370 | 23100 | 2.5 | 0.92 | (+) |
| Alg bulk | 6.0 | 3.40 | 1.8 | 7510 | 18700 | 2.5 | 0.95 | (+) |
| Alg bulk | 5.0 | 2.83 | 1.8 | 8920 | 16800 | 1.9 | 0.98 | (+) |
| Alg bulk | 4.6 | 2.6 | 1.8 | 6880 | 23500 | 3.4 | 0.90 | (+) |
| Alg bulk | 2.2 | 1.25 | 1.8 | 11000 | 42000 | 3.8 | 0.71 | (+) |
| Alg bulk | 2.0 | 1.13 | 1.8 | 13300 | 40400 | 3.0 | 0.73 | (+) |
| Alg bulk | 1.2 | 0.65 | 1.8 | 15000 | 67800 | 4.5 | 0.55 | (+) |
| Alg bulk | 0.5 | 0.28 | 1.8 | 23200 | 110500 | 4.7 | 0.46 | (+) |

[1]Weight fraction of polymer sample with average molecular weight $\leq$ 50 kD.
[2]Ionic cross-linking in 0.03 M $CaCl_2$ solution.

Example 13

High molecular weight alginate could be broken down into lower molecular weight fragments using various methods. Each method provided conditions resulting in alginates with molecular weights below 50 kD. In addition all alginate fragments still form gels in the presence of calcium ions. Based on its ease of use, gamma irradiation at 5.0 Mrad for 2.83 h was used to generate alginate fragments. Porous alginate beads were formed by the method described in the first part of this disclosure.

1.8% w:w alginate, 2.0M bicarbonate and 1.5% BSA were used as the starting solutions. 2 g of the alginate solution were mixed with 0.24 g of the BSA solution and 0.12 g of the bicarbonate solution to yield a foamy solution.

Example 14

We also investigated the use of other surfactants such as Pluronics F108 and F68. All surfactants yield a foamy solution and led to stable interconnected porous hydrogels.
1. 8% w:w alginate, 2.0M bicarbonate and 10% w:w solution of F108 were used as the starting solutions. 2 g of the alginate solution were mixed with 0.24 g of the F108 solution and 0.12 g of the bicarbonate solution to yield a foamy solution.
2. 8% w:w alginate, 2.0M bicarbonate and 1.5% w:w solution of F68 were used as the starting solutions. 2 g of the alginate solution were mixed with 0.24 g of the F68 solution and 0.12 g of the bicarbonate solution did not yield a sufficient foamy solution.
3. 8% w:w alginate, 2.0M bicarbonate and 5% w:w solution of F68 were used as the starting solutions. 2 g of the alginate solution were mixed with 0.24 g of the F68 solution and 0.12 g of the bicarbonate solution to yield a foamy solution.

Example 15

The amount of surfactant needed to yield a foamy solution was also investigated utilizing F108 as the surfactant.
1. 8% w:w alginate, 2.0M bicarbonate and 10% w:w solution of F108 were used as the starting solutions. 2 g of the alginate solution were mixed with 0.12 g of the F108 solution and 0.12 g of the bicarbonate solution to yield a foamy solution.
2. 8% w:w alginate, 2.0M bicarbonate and 10% w:w solution of F108 were used as the starting solutions. 2 g of the alginate solution were mixed with 0.06 g of the F108 solution and 0.12 g of the bicarbonate solution to yield a foamy solution.
3. 8% w:w alginate, 2.0M bicarbonate and 10% w:w solution of F108 were used as the starting solutions. 2 g of the alginate solution were mixed with 0.03 g of the F108 solution and 0.12 g of the bicarbonate solution. This composition did not result in a stable and sufficient foamy solution.

Example 16

The porosity of these beads was also investigated as described in Examples 4 and 5. Furthermore, environmental scanning electron microscopy (ESEM) was used to gain information regarding the porosity of the alginate beads. The samples were examined wet at the saturation vapor pressure of water vapor. ESEM data were obtained from the surface of the sample and their cross-sections. Further, overall porosity was determined.

The interconnected pore structure of the alginate beads formed from alginate fragments ($N_N$=8920, $M_w$=16800) was assessed by seeding a solution of suspended cells onto porous alginate beads, and subsequently visualizing these cells using a MTT (3-(4,5-dimethylthiazol-2-yl-2,5-diphenyl tetrazolium bromide) assay. In brief, 3T3 fibroblasts were suspended in Dulbecco's Modified Eagles Medium (2 million cells/ml). Alginate beads were removed from their aqueous solution, and blotted onto paper to allow the water within the pores to be removed by capillary action. The beads were then placed in the cell suspension. After 1 hour, beads were removed from the cell suspension, and washed with medium. The beads were placed in medium containing 0.5 mg/ml MTT. MTT is taken up by cells and reduced in the mitochondria to an insoluble blue product that can be readily visualized with microscopic examination. Non-porous beads will not take up cells and thus no stained cells will be present within beads that do not contain large pores (greater than approximately 10 microns in diameter). Matrices which are porous will take up cells and the distribution of dyed cells allows confirmation of the amount of interconnected pores in the matrix. All beads showed a high degree of cell incorporation with a uniform cell distribution throughout the entire bead.

To determine if the pore structure remained intact in vivo, porous alginate beads fabricated from alginate fragments ($M_N$=8920, $M_w$=16800) were transplanted into subcutaneous pockets of rats. The beads were harvested after 1 and 2 weeks, fixed, sectioned and stained with hematoxylin and eosin. Invasion of macrophages and fibroblasts was noted throughout the matrices at one week, with more cells being present and greater new collagen deposition in the beads by the invading cells by two weeks. This result confirms that the porous beads maintained their structure and allowed cell invasion in vivo. The beads maintained their original shape and dimensions, indicating that their mechanical properties were sufficient to withstand the compressional forces exerted in vivo.

Surface porosity of alginate beads was quantified by ESEM as follows:

Materials

8% Low molecular alginate (2 g/vial)

2 M NaHCO$_3$ (120 mg/vial)

Surfactant

10% w:w Pluronics F108 Prill (varied mg/vial) or

1.5% w:w BSA (240 mg/vial)

TABLE 7

| Surfactant % (w:w) | Surface Porosity (%) |
|---|---|
| 1.02 (F108) | 2.39 ± 0.61 |
| 0.54 (F108) | 20.97 ± 0.88 |
| 0.28 (F108) | 5.07 ± 0.40 |
| 0.15 (BSA) | 17.41 ± 1.80 |

Determination of overall bead porosity was conducted as follows:

calculate theoretical volume of a solid alginate bead

(4/3) Pi R$^3$=(4/3) Pi (1.5)$^3$=14 mm$_3$ lyophilize porous alginate beads weigh dry alginate beads $$(V_{solid\ bead} - V_{dry\ porous\ bed})/V_{solid\ bead} = \%\ \text{overall bead porosity}$$

TABLE 8

| Surfactant | Amount (mg) | % Porosity | Std. Deviation |
|---|---|---|---|
| 10% Pluronics F108 Prill | 240 | 41.6 | 2.9 |
| 10% Pluronics F108 Prill | 120 | 70.0 | 1.1 |
| 10% Pluronics F108 Prill | 60 | 46.5 | 1.1 |
| 1.5% BSA | 240 | 46.0 | 3.4 |

Experimental for Examples 17–20
Degradation of sodium alginate (MVG)

MVG with a number average molecular weight ($M_n$) of $1.7 \times 10_5$ and a polydispersity index (PDI) of 2.3 was broken down into lower molecular weight fragments utilizing gamma ($\gamma$)-irradiation. Alginate powder was irradiated using a cobalt-60 source for 2.83 h at a gamma dose of 5.0 Mrad. The molecular weights and corresponding weight fractions were determined using GPC.

Porous Beads

Preparation: An aqueous alginate solution (prepared from MVG or alginate fragments), a surfactant (0.15% (w/w) BSA or 0.14–1.02% (w/w) F108), and 0.9% (w/w) sodium bicarbonate were stirred to incorporate air until a stable foam (2-phase liquid/gas system) was obtained and the volume was about doubled (~30 min). The various concentrations of surfactant are shown in Table 9. The alginate concentration in the solution utilized to form beads was 1.75% (w/w) for non-degraded alginate and 7% (w/w) for low molecular alginate. Beads were then formed by the drop-wise extrusion of the foam into a 0.1 M $CaCl_2$ solution containing 10% (v/v) acetic acid. The acetic acid and sodium bicarbonate react to release carbon dioxide ($NaHCO_3 + CH_3COOH \rightarrow CH_3COONa + H_2O + CO_2 \uparrow$). The beads were collected, washed in deionized water, and subsequently exposed to vacuum at <400 Pa. Before exposure to the vacuum, the gas is contained in the beads in mostly closed pores with few openings to the surface. The vacuum draws the gas out leaving an open pore structure with many openings to the surface.

Porosity: The porosity of the beads was assessed utilizing three different methods. The first method to determine surface porosity utilized environmental scanning electron microscopy (ESEM) (ElectroScan Model E3, FEI Company, Hillsboro, Oreg.). The samples were examined while hydrated at the saturation pressure of water vapor (665 Pa, 5° C.). ESEM data were obtained for the surface and cross-sections of beads, and the porosity was calculated using computerized image analysis (Scion Image,, Version 1.62). Three batches of beads were fabricated to determine the variation in porosity within and between batches. The volume of pores within beads which were interconnected and accessible to the surface (i.e., surface accessible interconnected porosity) was determined next by measuring the total volume of porous beads and the amount of solvent required to fill the porous component. In brief, individual beads were placed in a graduated cylinder filled with a know volume of ethanol ($V_1$). The total volume following bead immersion was recorded ($V_2$). The beads were removed with the entrapped solvent in the pores, and the remaining volume of ethanol in the graduated cylinder was denoted ($V_3$). The total volume ($V_T$) of the beads was calculated according to eq. (1).

The surface accessible interconnected porosity $\chi$ was determined using eq. (2).

$$\chi = \frac{(V_1 - V_3)}{V_T} \times 100 \qquad (2)$$

The final method was used to determine the overall porosity or total void volume $$V_T = V_2 - V_3 \qquad (1)$$

($\epsilon$) of the beads by comparing the weight of porous beads to solid beads. Experimentally generated porous beads were measured to determine their radius (r) and subsequently dried to determine their mass ($m_p$): Next, the theoretical mass of a solid bead ($m_s$) with the same diameter was determined using the measured bead radius ($V = 4/3 \pi r^3$) and a composite density of 1 g/ml, which is a theoretical density based on the reason that the gels are greater than 90% water. The void volume was calculated utilizing eq. (3).

$$\varepsilon = \frac{(m_s - m_p)}{m_s} \times 100\% \qquad (3)$$

TABLE 9

Interconnected pore volume (%) and total pore volume (%) of macroporous beads.

| Surfactant (%) | Interconnected Pores (%) | Void Volume (%) |
| --- | --- | --- |
| 0.15 (BSA)[1] | 39 ± 1 | 78 ± 3 |
| 0.15 (BSA)[2] | 41 ± 1 | 46 ± 3 |
| 1.02 (F108)[2] | 36 ± 3 | 42 ± 3 |
| 0.54 (F108)[2] | 54 ± 2 | 74 ± 1 |
| 0.28 (F108)[2] | 45 ± 2 | 47 ± 1 |
| 0.14 (F108)[2] | —[3] | —[3] |

[1]beads were formed with MVG-alginate (2% (w/w)).
[2]beads were formed with low molecular weight alginate (8% (w/w)).
[3]no foam was formed.

MTT assay: The interconnected pore structure of the matrices was assessed qualitatively by seeding a solution of suspended cells onto porous alginate beads and subsequently visualizing these cells using the MTT (3-(4,5-dimethylthiazol-2-yl-2,5-diphenyl tetrazolium bromide) assay. In brief, 3T3 fibroblasts were suspended in DMEM (2 million cells/ml). Alginate beads were removed from their aqueous solution and blotted onto paper to allow the water within the pores to be removed by capillary action. The beads were then placed in the cell suspension. After 1 hour, beads were removed from the cell suspension and washed with medium. The beads were placed in medium containing 0.5 mg/ml MTT. MTT is taken up by cells and reduced in the mitochondria to an insoluble blue product that can be readily visualized with microscopic examination. Non-porous beads will not take up cells, and thus, no stained cells will be present within beads that do not contain large pores (greater than approximately 10 $\mu$m in diameter). Matrices that are porous will take up cells, and the distribution of dyed cells allows confirmation of the amount and homogeneity of interconnected pores in the matrix.

In vivo experiments: Porous alginate beads were implanted into subcutaneous pockets created using a purse string procedure (Greene et al., The purse string model as a method of implanting and localizing cellular constructs. Proceedings of the Third North Carolina Tissue Engineering Group Meeting, 1999, Charlotte, N.C.) The pocket was first outlined with a running suture placed in a circular path on the back of a 100–150 g Lewis rat (Charles River). The two ends of the suture were subsequently pulled taut and tied, thus forming a self-contained, stable pocket. A small incision was made at the top of the pocket and porous alginate beads were implanted. The incision was subsequently sutured to close. Implants were retrieved two weeks post-implantation, fixed in 10% neutral buffered formalin, dehydrated, and embedded in paraffin using standard procedures. Sections were then cut, mounted, and stained with hemnatoxylin and eosin. All animal procedures were performed according to the guidelines established by the University Committee on the Use and Care of Animals.

Example 17

An initial set of experiments was used to determine a range of conditions suitable for the formation of porous matrices. A mixture comprised of 1.75% (w/w) MVG alginate, 0.15% (w/w) BSA, and 0.9% (w/w) NaHCO$_3$ yielded a stable foam that subsequently was utilized to form porous beads with an interconnected pore structure. Using electron microscopy, the interior of the beads showed a more interconnected, open pore structure than the surface. The total pore volume was calculated to be 78±3% and the interconnected, surface accessible porosity was determined to be 39±1%. The difference between these porosity measurements is due to pores that have a closed structure with no interconnection to the exterior surface of the beads. To confirm the interconnected pore structure of the beads, cells were seeded into the beads and stained to highlight their distribution by the MTT assay. Fibroblasts were found to evenly distribute throughout the entire bead at this level of examination.

Example 18

Figure 1A:
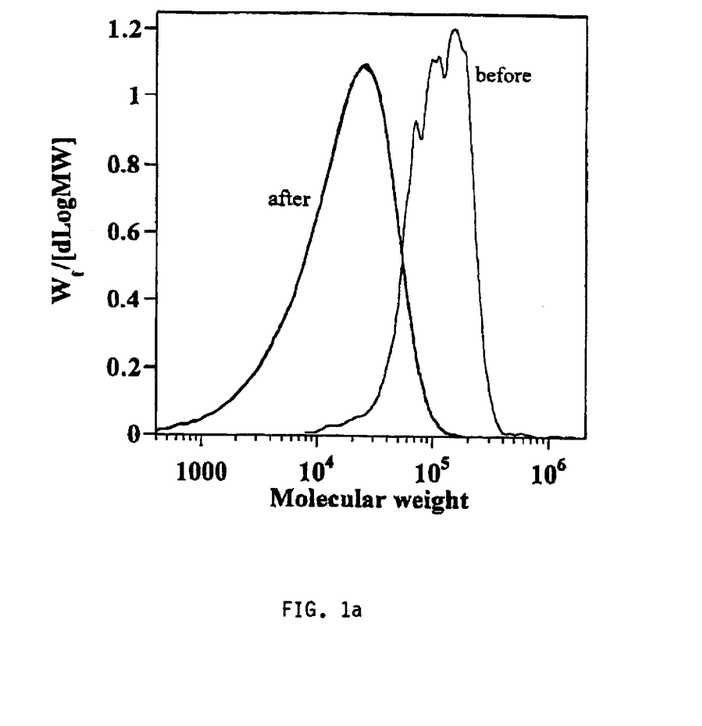
Figure 1B:
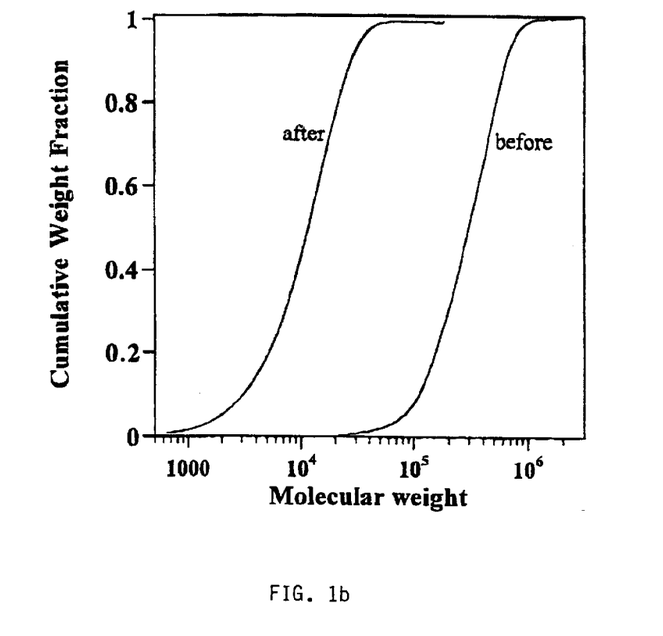

Beads were prepared from a low molecular weight alginate. First a commercially available alginate powder ($M_N$=170 kD, PDI=2.3) was γ-irradiated at a dosage of 5 Mrad for 2.83 hr. These conditions led to alginate fragmentation and polymer chains with greatly decreased molecular weights ($M_N$=9,370 Daltons, PDI=2.5), 92% of which had molecular weights less than 50 kD. The molecular weight distributions and fractions before and after such treatment are shown in FIGS. 1a and 1b, respectively. Despite the substantially lower molecular weights of these alginate fragments, they still formed three-dimensional networks in the presence of $Ca^{2+}$-ions. The alginate fragments were formed into porous beads utilizing the procedure described above. The only change made was the use of 7% (w/w) alginate instead of 1.75% (w/w) solution. The percentage of interconnected pores was comparable for beads prepared from the high (39±1%) and the low (41±1%) molecular weight alginate. However, the overall void volume was significantly higher in beads prepared with the high molecular weight alginate (78±3%) compared to the lower molecular weight alginrate (46±3%).

Example 19

The role of the surfactant, which stabilizes the gas foam during the process, was examined. It was of particular interest in this work to replace BSA with other suitable surfactants, as residual BSA remaining in the beads following processing could possibly lead to an inflammatory response following implantation. Block copolymers composed of poly(ethylene oxide)-poly(propylene oxide-poly (ethylene oxide) (Pluronics F108 and F68) were used in place of BSA, as these surfactants are widely utilized in a variety of biological applications. Both surfactants were capable of stabilizing the gas foam during processing and could be used to form porous beads from the low molecular weight alginate. Utilization of Pluronics F108 resulted in increased porosity of the corresponding beads, and this surfactant was utilized in all future studies. The amount of F108 was varied (0.14–1.02%) to study how different amounts of surfactant effected the porosity of beads. A concentration of 0.54% (w/w) F108 resulted in beads exhibiting the highest interconnected pore volume (54±2%) and overall pore volume (74±1%) (Table 9). The interconnected pore structure was again verified by seeding fibroblasts into the beads and visualizing the cells utilizing the MTT assay. A uniform cell distribution was again noted throughout the entire bead volume, confirming the interconnected pore structure of the beads.

Example 20

A test of one utility of these structures involves determining if the pore structure remained intact in vivo and allowed cell invasion. To test this, porous alginate beads fabricated from low molecular weight alginate, using F108 as surfactant, were transplanted into subcutaneous pockets in vivo. Importantly, the beads maintained their porous structure and allowed cell invasion in vivo. Invasion of macrophages and fibroblasts was noted throughout. the matrices after two weeks of implantation. Additionally, blood vessels containing erythrocytes were observed in the polymer interior thus demonstrating that the pores were large enough to allow vascularization of the alginate bead. The presence of granulation tissue through the interior of the matrix is consistent with an interconnected network of pores.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A method for preparing a hydrogel material having macroporous open pore porosity, which comprises:
    a) providing a solution of a hydrogel-forming material, a surfactant and, optionally, a gas-generating component, which solution is capable of being mixed in the presence of a gas to incorporate the gas in the solution and form a stable foam;
    b) forming a stable foam by mixing the solution in the presence of a gas and/or, if the gas-generating component is present, by subjecting the solution to conditions or agents which result in generation of gas from the gas-generating component;
    c) exposing the stable foam to conditions and/or agents which result in gelling of the hydrogel-forming material to form a hydrogel containing gas bubbles therein;
    d) releasing the gas bubbles from the hydrogel to form a hydrogel material having macroporous open pore porosity.

2. The method of claim 1, wherein the hydrogel is an alginate hydrogel.

3. The method of claim 1, wherein the hydrogel-forming material is an alginate solution, the surfactant is BSA, a gas-generating component which is sodium bicarbonate is used and a solution of calcium chloride and acetic acid in water is used as the gelling agent and agent for generation of gas from the gas-generating component, respectively.

4. The method of claim 3, wherein the alginate solution is a solution of 3 to 5% w:w sodium alginate, the BSA is provided as a 1.0 to 10 weight percent solution in water and the sodium bicarbonate is provided as a 1.0M to 2.0M solution, wherein the BSA solution and sodium bicarbonate solution are combined with the alginate in a weight ratio of the BSA solution to the sodium bicarbonate solution from 2:1 to 1:1, and wherein the solution of calcium chloride and acetic acid in water has a calcium chloride concentration from 0.1 to 1.0M and an amount of acetic acid of about 10 volume %.

5. The method of claim 2, wherein the alginate is an alginate having a reduced molecular weight of 1600 to 80,000 daltons.

6. The method of claim 1, wherein the surfactant is BSA, a pluronic surfactant or a propylene glycol alginate surfactant.

7. The method of claim 1, wherein the solution contains a gas-generating component.

8. The method of claim 1, wherein the stable foam is exposed to the conditions and/or agents which result in gelling of the hydrogel-forming material by dropwise addition through a syringe opening into a gelling solution to form microbeads.

9. The method of claim 3, wherein the stable foam is exposed to the conditions and/or agents which result in gelling of the hydrogel-forming material by dropwise addition through a syringe opening into a gelling solution to form microbeads.

10. The method of claim 8, wherein the dropwise addition is conducted with a syringe pump.

11. The method of claim 3, wherein the solution to be mixed to form a stable foam contains 3–10% weight of alginate, 0.05–1.0% weight BSA and 0.5 to 5.0% weight of sodium bicarbonate.

12. The method of claim 2, wherein the alginate is an alginate having a reduced molecular weight of 8,000 to 50,000 daltons.

13. The method of claim 1, wherein the surfactant is a pluronic surfactant.

14. The method of claim 12, wherein the surfactant is a pluronic surfactant.

15. The method of claim 1, wherein the releasing of the gas bubbles, step (d), is conducted by exposing the hydrogel to a vacuum.

16. The method of claim 7, wherein the gas-generating component is sodium bicarbonate.

17. The method of claim 1, wherein steps b) and c) are conducted substantially simultaneously.

* * * * *

UNITED STATES PATENT AND TRADEMARK OFFICE
CERTIFICATE OF CORRECTION

PATENT NO. : 6,511,650 B1
DATED : January 28, 2004
INVENTOR(S) : Petra Eisett et al.

It is certified that error appears in the above-identified patent and that said Letters Patent is hereby corrected as shown below:

Column 18,
Line 61, reads "1,600" should read -- 1,000 --

Column 20,
Line 2, reads "8,000" should read -- 1,000 --

Signed and Sealed this

Seventh Day of September, 2004

JON W. DUDAS
*Director of the United States Patent and Trademark Office*